US00PP33494P3

(12) United States Plant Patent
Mazzardis

(10) Patent No.: US PP33,494 P3
(45) Date of Patent: Sep. 21, 2021

(54) BLUEBERRY PLANT NAMED 'NS 16-18'

(50) Latin Name: ***Vaccinium* hybrid**
Varietal Denomination: NS 16-18

(71) Applicant: Next Progeny Pty., Ltd., Subiaco (AU)

(72) Inventor: Vincent David Andrew Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 17/107,074

(22) Filed: Nov. 30, 2020

(65) Prior Publication Data

US 2021/0227738 P1 Jul. 22, 2021

(30) Foreign Application Priority Data

Jan. 22, 2020 (QZ) ..... PBR 2020/0192

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368
See application file for complete search history.

*Primary Examiner* — Anne Marie Grunberg
(74) *Attorney, Agent, or Firm* — Randall Danskin, P.S.

(57) ABSTRACT

A new and distinct variety of blueberry plant, which is denominated varietally as 'NS 16-18' is described, with a weak to medium plant vigor and which produces fruit considered large to very large in size, medium in sweetness, and firm to very firm under the ecological conditions prevailing in Yanchep, Western Australia.

2 Drawing Sheets

Latin name: *Vaccinium* hybrid.

Variety denomination: The invention relates to a new, novel, and distinct variety of blueberry plant, a *Vaccinium* hybrid, with a variety denomination hereinafter as 'NS 16-18'.

CROSS REFERENCE TO RELATED APPLICATIONS

This application claims the benefit of priority under 35 USC § 119 to Community Plant Variety Office (CPVO) Application No. 2020/0192 for Community Plant Variety Rights, filed on Jan. 22, 2020 for a blueberry plant with a variety denomination of 'NS 16 18', which is herein incorporated by reference in its entirety.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, cross-pollinations were made in order to produce plant populations from which improved progeny were evaluated and thereafter selected.

The 'NS 16-18' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant 'EB 9-4' (U.S. Plant Pat. No. 28,334), and a pollen parent, blueberry plant 'EB 8-50' (U.S. Plant Pat. No. 28,357) during the 2013 growing season.

Prior Varieties. The seed parent 'EB 9-4' is characterized principally by a semi-upright to intermediate growth habit, a medium vigor, a very early season first pick date, and further produces large- to very-large-sized, firm, high sweetness, and low to medium acidity fruit under the ecological conditions occurring in Yanchep, Western Australia. Also, the seed parent 'EB 9-4' exhibits a very early date of bloom time, a medium fruit cluster density, and a last pick date in February of the following year under the ecological conditions occurring in Yanchep, Western Australia. Further, the seed parent 'EB 9-4' is evergreen and produces fruit on one-year-old and current season's shoots.

The pollen parent 'EB 8-50', on the other hand, is characterized principally by a semi-upright to intermediate growth habit, a medium vigor, a very early season first pick date, and further produces large- to very-large-sized, firm to very firm, high to very high sweetness, and low acidity fruit under the ecological conditions occurring in Yanchep, Western Australia. Also, the pollen parent 'EB 8-50' exhibits a very early date of bloom time, a dense fruit cluster density, and a December last pick date under the ecological conditions occurring in Yanchep, Western Australia. Further, the pollen parent 'EB 8-50' is evergreen and produces fruit on one-year-old and current season's shoots.

Origin. The seed from the seed parent 'EB 9-4' produced approximately 1,100 plants following cross-pollination. These new plants were then grown at the aforementioned property, and fruit from these new plants was first observed in 2015. A subsequent assessment of these same self-fertile, new plants conducted during the 2016 growing season led to selecting the 'NS 16-18' variety for additional evaluation in 2017, which led to selection for further evaluation.

Asexual Reproduction. The further evaluation included an asexual vegetative propagation, by vegetative cuttings, at Yanchep Springs in Yanchep, Western Australia. Subsequent evaluations of the newly derived plants in the 2018 growing season led to a conclusion that the 'NS 16-18' variety was a distinct and new variety of blueberry plant found to be true to the original plant. The new variety of blueberry plant was considered to be novel in view of its weak to medium plant vigor, large to very large fruit size, medium fruit sweetness, and firm to very firm fruit.

Comparisons. In comparison to the seed parent 'EB 9-4' under the ecological conditions occurring in Yanchep, Western Australia, the new variety is noteworthy. In this regard, the seed parent has a plant vigor considered to be medium. In contrast, the new variety of blueberry plant has a plant vigor considered to be weak to medium. In addition, the seed parent and the new variety of blueberry plant both produce fruit with a size considered to be large to very large. Also, the seed parent produces fruit considered to be high in sweetness. This is in contrast to the fruit of the new variety of blueberry plant, which is considered to be medium in sweetness. Further, the seed parent produces fruit considered to be firm. This is in contrast to the fruit of the new variety of blueberry plant, which is considered to be firm to very firm.

In comparison to the pollen parent 'EB 8-50' under the ecological conditions occurring in Yanchep, Western Australia, the new variety is noteworthy. In this regard, the pollen parent has a plant vigor considered to be medium. In contrast, the new variety of blueberry plant has a plant vigor considered to be weak to medium. In addition, the pollen parent and the new variety of blueberry plant both produce fruit with a size considered to be large to very large. Also, the pollen parent produces fruit considered to be high to very high in sweetness. This is in contrast to the fruit of the new variety of blueberry plant, which is considered to be medium in sweetness. Further, the pollen parent and the new variety of blueberry plant both produce fruit considered to be firm to very firm.

The new variety of blueberry plant is readily distinguishable from the most closely related, known variety, the 'EB 12-3' blueberry plant described in Australia Plant Breeder Right 2017/316, filed Oct. 31, 2017, titled "Southern Highbush Blueberry (*Vaccinum* hybrid) Variety EB 12-3," which is herein incorporated by reference in its entirety. In this regard, the closest known variety 'EB 12-3' has a plant vigor considered to be strong. In contrast, the new variety of blueberry plant has a plant vigor considered to be weak to medium. In addition, the closest known variety 'EB 12-3' produces fruit with a size considered to be large. This in contrast to the fruit of the new variety of blueberry plant, which is considered to be large to very large in size. Also, the closest known variety 'EB 12-3' produces fruit considered to be medium to high in sweetness. This is in contrast to the fruit of the new variety of blueberry plant, which is considered to be medium in sweetness. Further, the closest known variety 'EB 12-3' produces fruit considered to be medium in firmness. This is in contrast to the fruit of the new variety of blueberry plant, which is considered to be firm to very firm.

The comparisons described above are summarized in Table 1 below.

TABLE 1

Summary of Comparisons

| | 'NS 16-18' | 'EB 12-3' | 'EB 9-4' (Seed) | 'EB 8-50' (Pollen) |
|---|---|---|---|---|
| Plant vigor | Weak to medium | Strong | Medium | Medium |
| Fruit size | Large to very large | Large | Large to very large | Large to very large |
| Fruit sweetness | Medium | Medium to high | High | High to very high |
| Fruit firmness | Firm to very firm | Medium | Firm | Firm to very firm |

In addition, Table 2 below compares the 'NS 16-18' variety to a sibling cultivar that resulted from same the seed parent 'EB 9-4' and pollen parent 'EB 8-50', namely, 'NS 16-2' (U.S. Plant Pat. No. 32,897).

TABLE 2

Comparison to Sibling Cultivar

| | 'NS 16-18' | 'NS 16-2' |
|---|---|---|
| Plant vigor | Weak to medium | Medium |
| Fruit size | Large to very large | Very large |
| Fruit sweetness | Medium | Medium to high |
| Fruit firmness | Firm to very firm | Very firm |
| Fruit acidity | Medium to high | Low |

BRIEF DESCRIPTION OF THE DRAWINGS

The accompanying drawings are color photographs of the new blueberry plant 'NS 16-18' during the second year of growth under the ecological conditions prevailing at the breeder's property, which is located at Yanchep Springs in Yanchep, Western Australia.

Figure 1:
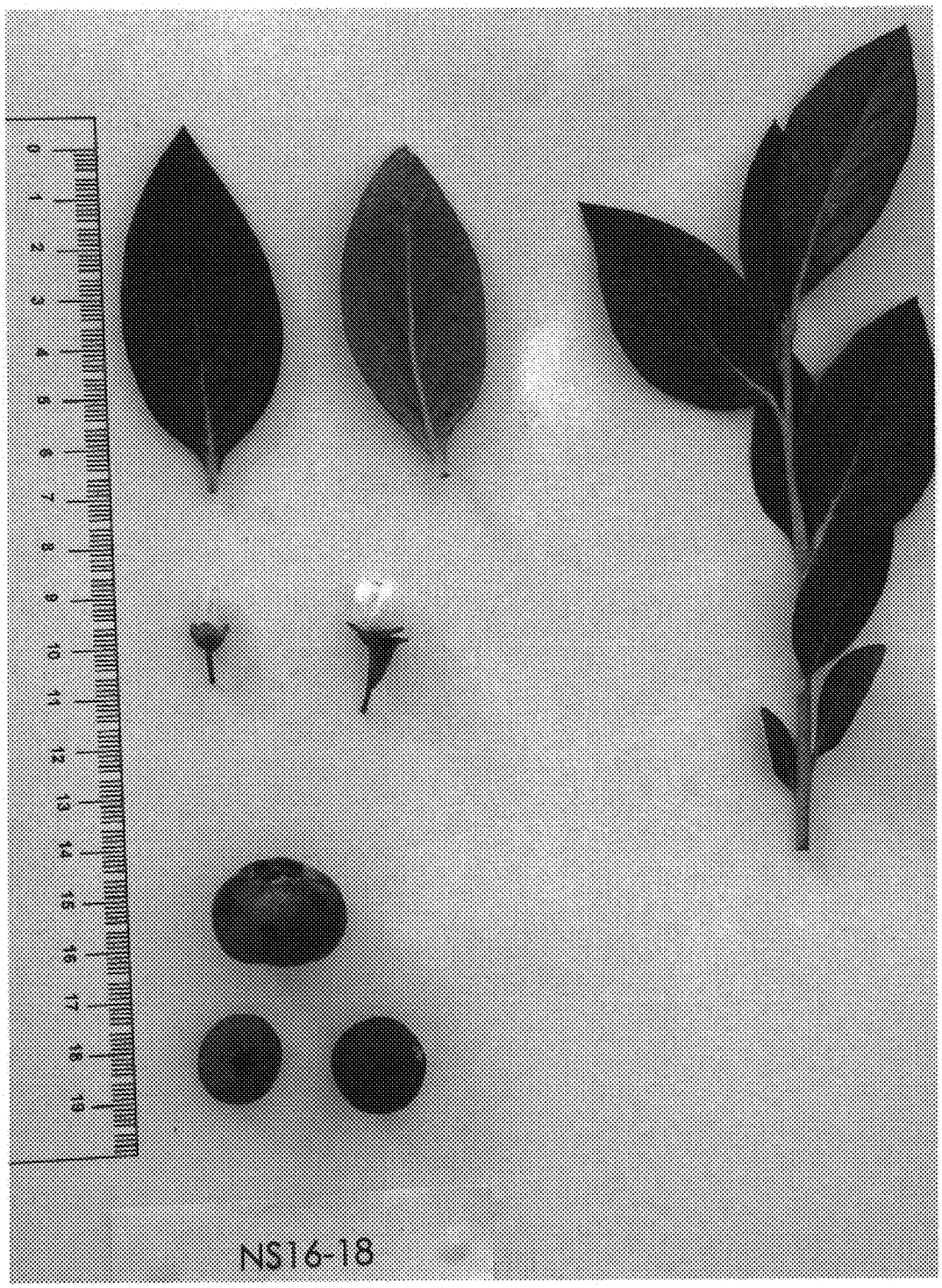
FIG. 1 is a color photograph, which shows fruit, blooms, leaves, and a portion of a vegetative stem of the new blueberry plant 'NS 16-18', the fruit being sufficiently mature for harvesting and shipment. This photograph also depicts the fruit size and the color of the ripe fruit, two leaves showing the sizes and the upper and under side colorations thereof, two blooms at different stages of maturation, and additional leaves on the stem at different stages of maturation.
Figure 2:
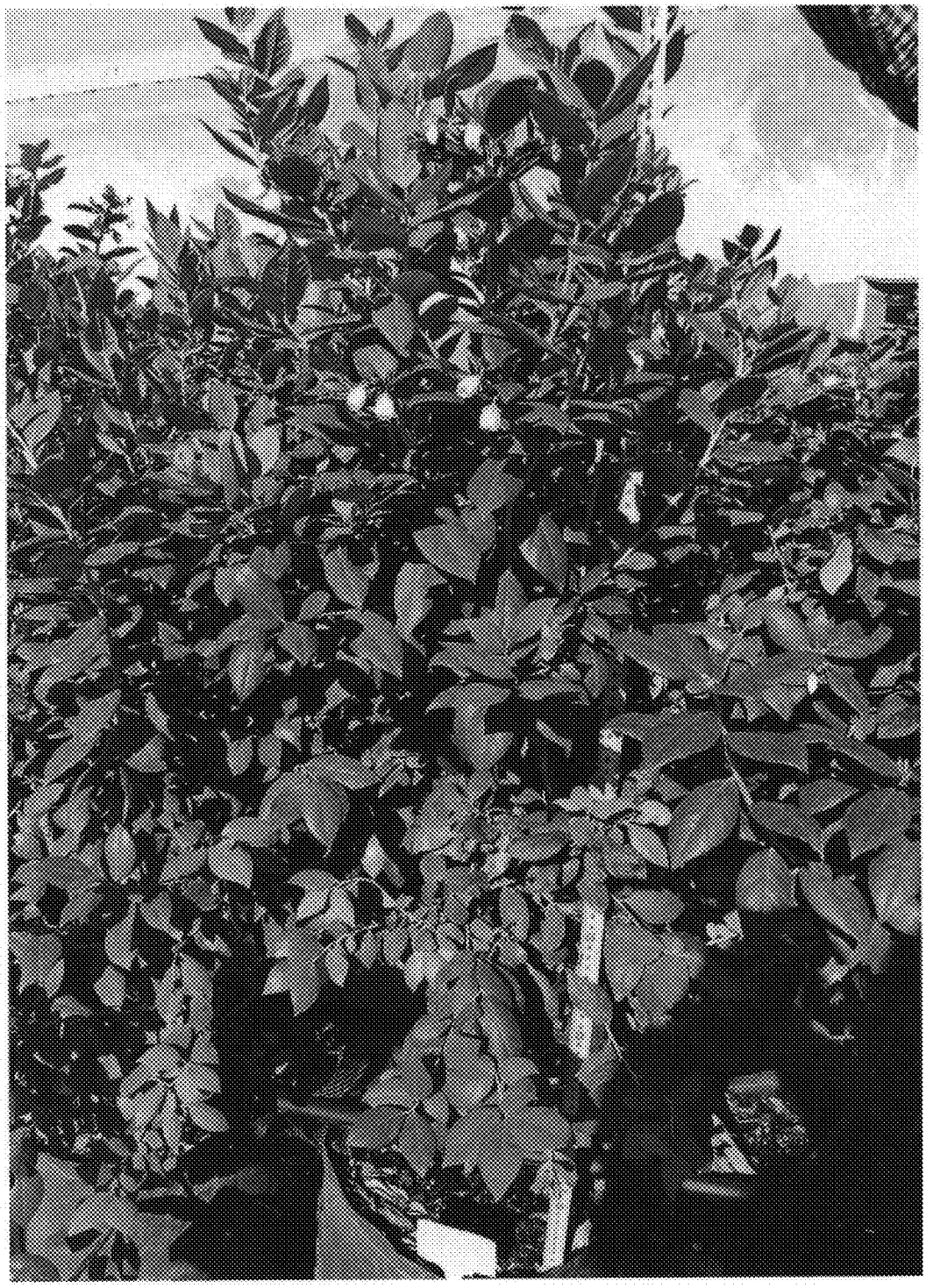
FIG. 2 is a color photograph, which shows the new blueberry plant 'NS 16-18.' This photograph depicts a mature bush with ripe and unripe fruits, the fruit size, and the upright growth habit of the bush. The ripe fruit is sufficiently mature for harvesting and shipment.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition (2015), hereinafter, "R.H.S.") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the second year of growth under the ecological conditions prevailing at the breeder's property, which is located at Yanchep Springs in Yanchep, Western Australia.

Plant: General.

*Vigor*.—Considered weak to medium for the species. This is in contrast to the seed parent 'EB 9-4' and the pollen parent 'EB 8-50', wherein the vigor is considered to be medium. This is also in contrast to the closest known variety 'EB 12-3', wherein the vigor is considered to be strong.

*Growth habit*.—Considered upright, in like manner to the commercial variety 'Ivanhoe' (unpatented).

*Average size of plant*.—1.0 meters in height by 0.56 meters in width.

*Internode length* (*space between nodes*).—Considered medium, 18.0 millimeters (mm).

*Bark color*.—RHS Dark Reddish Orange Group 175B.

*Color, one year old shoots*.—RHS Light Yellow Green Group 144D.

*Fruiting type*.—On one-year-old shoots and current season's shoots, in like manner to commercial varieties 'Concord' (unpatented) and 'Burlington' (unpatented).

Foliage: General.

*Average leaf length*.—Considered medium for the species, 55.0 mm.

*Average leaf width*.—Considered medium for the species, 26.5 mm.

*Color of leaf upper*.—RHS Moderate Olive Green Group 137B.

*Color of leaf underside*.—RHS Moderate Yellow Green Group 138B.

*Vein color of plant leaf*.—RHS Strong Yellow Green Group 145A.

*Venation pattern of leaf*.—Pinnate reticulate.

*Leaf apex texture*.—Glabrous.

*Leaf apex shape*.—Acute.

*Leaf base shape*.—Acute.

*Leaf shape*.—Elliptic.

*Leaf margin*.—Entire.

*Leaf arrangement of plant*.—Alternate.

*Petiole length*.—5.10 mm.

*Petiole diameter*.—1.72 mm.

*Petiole color*.—RHS Light Yellow Green 145B.

Flowers:

*Number of flowers/inflorescence*.—4.

*Length of inflorescence* (*excluding pedicel*).—Considered long to very long, 16 mm.

*Corolla shape*.—Urceolate.

*Corolla tube surface texture*.—Ridges are present on the corolla tube.

*Average corolla length*.—10 mm.

*Corolla diameter*.—8.4 mm.

*Corolla aperture size*.—4.48 mm.

*Corolla color*.—RHS White Group NN155C.

*Pedicel color*.—RHS Strong Yellow Green Group 144C.

*Pedicel length*.—9.77 mm.

*Average calyx diameter*.—Considered small to medium, 4.77 mm.

*Average calyx basin depth*.—Considered medium, 1.81 mm.

*Attitude of sepals*.—Erect.

*Type of sepals*.—Straight.

Reproductive organs:

*Size of pollen anthers*.—6.31 mm.

*Color of pollen anthers*.—RHS Brownish Orange Group 172C.

*Pistil length*.—9.35 mm.

*Pistil color*.—RHS Light Yellow Green Group 145C.

Fruit:

*Color of unripe fruit*.—RHS Strong Yellow Green Group N144A.

*Color of fruit skin*.—RHS Bluish Black Group 203C, also considered "dark blue" in like color to the commercial variety 'Heerma' (unpatented), after removal of bloom.

*Color of ripe fruit flesh*.—RHS Light Yellow Green Group 145C.

*Color of seeds*.—RHS Dark Reddish Orange Group 175C.

*Average fruit size*.—Large to very large, 21 mm in diameter and 16.34 mm in height. This is comparable to the seed parent 'EB 9-4' and the pollen parent 'EB 8-50', wherein the fruit size is also considered large to very large. This is in contrast to the closest known variety 'EB 12-3', wherein the fruit size is considered large.

*Average weight of fruit*.—3.33 grams.

*Berry shape*.—Considered oblate.

*Sweetness when ripe*.—Considered medium for the species. This is in contrast to the seed parent 'EB 9-4', wherein the fruit sweetness is considered high. This is also in contrast to the pollen parent 'EB 8-50', wherein the fruit sweetness is considered high to very high. This is further in contrast to the closest known variety 'EB 12-3', wherein the fruit sweetness is considered medium to high.

*Firmness when ripe*.—Considered firm to very firm for the species. This is comparable to the pollen parent 'EB 8-50', wherein the fruit firmness is also considered firm to very firm. This is in contrast to the seed parent 'EB 9-4', wherein the fruit firmness is considered firm. This is also in contrast to the closest known variety 'EB 12-3', wherein the fruit firmness is considered medium.

*Acidity when ripe*.—Considered medium to high for the species.

*Cluster density*.—Considered sparse for the species.

*Average fruit production.*—2 kilograms on a two-year-old bush.

*Storability of fruit.*—Considered excellent for the species.

*Market use of fruit.*—1st grade fresh market fruit.

*Date of bud burst.*—This variety is evergreen under the ecological conditions prevailing in Yanchep, Western Australia, but a bud break occurs in late June.

*Date of bloom time.*—This variety is evergreen under the ecological conditions prevailing in Yanchep, Western Australia, but a bloom time occurs at the end of July, which is considered early on one-year-old shoot in like manner to the commercial variety 'Weymouth' (unpatented) and is considered early on current year's shoot in like manner to the commercial variety 'O'Neal' (unpatented).

*Duration of bloom time.*—6 weeks.

*Beginning of fruit ripening.*—Considered early on one-year-old shoot in like manner to the commercial variety 'Blueray' (unpatented) and early on current year's shoot in like manner to the commercial variety 'O'Neal' (unpatented).

*First pick date.*—The observed date of the first pick is approximately October under the ecological conditions prevailing in Yanchep, Western Australia.

*Last pick date.*—The observed date of the last pick is approximately December under the ecological conditions prevailing in Yanchep, Western Australia.

*Pollination requirements.*—Self-fertile.

*Resistance to pests and disease.*—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a plant Letters Patent is:

1. A new and distinct variety of blueberry plant, substantially as illustrated and described, which is characterized principally as to novelty by a weak to medium plant vigor and by producing fruit considered large to very large in size, medium in sweetness, and firm to very firm under the ecological conditions prevailing in Yanchep, Western Australia.

* * * * *